United States Patent [19]

Mutzhas

[11] 4,444,190

[45] Apr. 24, 1984

[54] DEVICE FOR THE PHOTOTHERAPEUTIC TREATMENT OF HYPERBILIRUBINEMIA

[76] Inventor: Maximilian F. Mutzhas, Sonnenstr. 17, D-8000 Müchen 2, Fed. Rep. of Germany

[21] Appl. No.: 319,454

[22] Filed: Nov. 9, 1981

[30] Foreign Application Priority Data

Nov. 24, 1980 [DE] Fed. Rep. of Germany ....... 3044184

[51] Int. Cl.³ .............................................. A61N 5/00
[52] U.S. Cl. ................................. 128/396; 250/503.1; 250/504 R
[58] Field of Search ............... 128/395, 396, 373, 374; 250/503.1, 504 R

[56] References Cited

U.S. PATENT DOCUMENTS

| 3,658,068 | 4/1972 | McNall | 128/395 |
| 3,822,706 | 7/1974 | Simone et al. | 128/396 |
| 4,246,905 | 1/1981 | Corth | 128/395 |

FOREIGN PATENT DOCUMENTS 2714724 10/1978 Fed. Rep. of Germany ...... 250/504

Primary Examiner—Lee S. Cohen
Attorney, Agent, or Firm—Learman & McCulloch

[57] ABSTRACT

The disclosure concerns a device for the phototherapeutic treatment of hyperbilirubinemia in newborn infants by radiation. This device ensures that at most 10% of the radiation present in the effective range of 405 to 545 nm lies below 460 nm. Adverse effects associated with the presence of radiation of wavelengths shorter than 460 nm in the known devices are thereby avoided.

24 Claims, 5 Drawing Figures

DEVICE FOR THE PHOTOTHERAPEUTIC TREATMENT OF HYPERBILIRUBINEMIA

The invention concerns a device for the phototherapeutic treatment of hyperbilirubinemia in new born children by irradiation.

Hyperbilirubinemia, which occurs comparatively frequently in new-born, and particularly prematurely born, infants, is the condition of excessive bilirubin, the essential gallbladder dye ($C_{33}H_{33}O_6N_4$), in the blood. One of its causes is the not yet fully developed functioning of the liver in the newborn's blood circulatory system. Because of the reduced liver function, the fat-soluble bilirubin cannot be converted to the water-soluble products excretable in the urine. Hyperbilirubinemia also results in an increased permeability of the blood-brain barrier, so that newborns suffering from this condition are more susceptible to damage to the central nervous system caused by the decomposition products of bilirubin in the brain cells.

Up to now hyperbilirubinemia is being treated either with chemotherapy or with phototherapy. In the phototherapeutic treatment, the effective spectral region is considered, in line with BRD specification DIN 5,031 Part 10, to extend from about 400 nm to 550 nm (405 to 545 nm), the greatest effect being ascribed to radiation of wavelengths between approximately 450 and 460 nm. Up to now in phototherapy, either fluorescent lamps with a blue phosphor are in use, or lamps whose radiation extends over a large part of the visible spectrum, and which can thus be classified as white-light lamps. The spectrum of the blue-light fluorescent lamps extends from approximately 400 to 550 nm, and that of the white-light fluorescent lamps from about 300 to 780 nm.

Also used in the phototherapeutic treatment of hyperbilirubinemia are high-pressure-mercury-lamps, provided with an additional outer bulb whose inner side is coated with a phosphor having strong emission in the range of about 500 to 550 nm.

And finally, in technically less developed parts of the world, heliotherapy, using unfiltered sunlight as radiation source, is still used.

An underlying objectives of the invention is the provision of a new device for the phototherapeutic treatment of hyperbilirubinemia that will distinguish itself by its essentially improved effectiveness and at the same time by its avoidance of the dangers and damage associated with the known irradiation devices.

This objective is achieved in that with the new device for the phototherapeutic treatment of hyperbilirubinemia in newborn infants by irradiation, no more than 10% of the radiation in the effective range of 405 to 545 nm lies below 460 nm.

Thorough photobiological investigations, on which this invention is based, have shown that—contrary to the prevailing professional opinion—visible light from the blue spectral range (for example, in the presence of chromophores, such as riboflavin) can lead to cell damage (DNA), and that the maximum of the spectral injury function lies at about 450 nm, that is to say, very nearly at the point of the spectrum at which the relative spectral effectiveness function of the bilirubin dissociation (per DIN specification) has its maximum value. Cell damage (e.g., mutagenesis), as well as other injurious effects (of, for example, phototoxic type) to the skin, or eye injuries (blue-light hazard) can, however, be in part more dangerous than the injuries caused by the bilirubin itself. From these facts follows for the invention the recognition that that part of the radiation used in the treatment of hyperbilirubinemia which lies below about 460 nm should be suppressed as much as possible.

On the other hand, the extensive investigations leading to the invention have shown that radiation of wavelengths greater than about 480 to 490 nm can lead to a reversal of the isomerization of the water-soluble isomers. Radiation in this part of the spectrum thus leads to at least a partial reversal of the desired effect. From these facts follows for the invention the further recognition that that part of the radiation used in the treatment of hyperbilirubinemia which lies above about 480 nm should be suppressed as much as possible.

In apparatus according to the invention at least 50% of the radiation produced in the effective range of 405 to 545 nm lies between 460 and 480 nm. Practically, at least 50% of the entire radiation lies within this 460- to 480-nm range, and preferably, however, at least 90% of the entire radiation.

The irradiation in the range of 460 to 480 nm is at the irradiated area at least 2 $W/m^2$, and preferably 5 to 30 $W/m^2$.

Further essential features of the invention concern the type of radiators and filters used.

Thus, as a radiator may be used a low-pressure mercury-lamp (fluorescent lamp) coated with phosphor, a large part of whose radiation lies between 460 and 480 nm. Such a low-pressure mercury lamp is preferably coated with a phosphor composed essentially of barium-magnesium aluminate activated with europium and/or calcium fluorophosphate activated with antimony and/or calcium tungstate activated with lead and/or strontium pyrophosphate activated with tin and/or barium-titanium pyrophosphate and/or magnesium tungstate activated with tungsten and/or strontium fluorophosphate activated with antimony and manganese.

To raise the radiation output, such a low-pressure mercury lamp may be equipped with a reflecting coat applied to an inner or outer surface.

For the purpose of the invention, however, a radiator can be used, consisting of a low-pressure mercury lamp with phosphor coating containing an amalgam, preferably indium amalgam, in place of the elementary mercury, and having a high radiation output between 460 and 480 nm. Such a lamp can produce a higher output.

Corresponding to another embodiment of the invention, is a radiator, consisting of a high-pressure mercury lamp, doped with a cadmium halide and/or zinc halide and/or thulium halide and/or halides of other rare-earth elements. If cadmium halide, zinc halide, and/or thulium halide are used for doping, the amount of each used lies between 0.01 and 4 $mg/cm^3$. The iodide is the preferred halide in these applications.

Within the scope of this invention also fall high-pressure radiators containing no mercury, but filled with cadmium halide and/or zinc halide, and/or thulium halide. In such cases the amounts of each of these halides lies between 0.02 and 8 $mg/cm^3$. Iodides are the preferred halides in these cases.

For the suppresion of radiation lying below 460 nm, and, when called for, of components lying above 480 nm, a device in accordance with the invention contains at least one filter or filter system. The purpose is to provide at the irradiated area the highest possible fraction of radiation in the range 460 to 480 nm and to filter out as much as possible of the radiation lying outside this range, particularly below 460 nm.

Within the scope of this invention, absorption filters, interference filters, and suitable combinations of these filter types can be employed.

Absorption filters contain an admixture of materials which absorb radiation of the undesired wavelengths. In the case of glass filters, glass coloured by thermal treatment (such as Schott GG 475 3 mm) is used, in which sulfur- and/or cadmium sulfide is dissolved, for suppression of radiation of wavelengths below 460 mm; for the suppression of radiation above 480 nm, an absorption filter of glass with ionic coloration (such as Schott BG37 5 mm) containing dissolved nickel oxide and/or cobalt oxide is used.

If necessary, an additional, heat-absorbing filter can be incorporated to suppress any remaining infrared radiation, in order to keep the burden on the newborn as low as possible (for example Schott KG1 6 mm). However, absorption filters of synthetic materials can also be used. The basic material in this case is a transparent synthetic (polymeric methyl methacrylate (PMMA), polycarbonate, polyester, PVC, polystirol, etc.). The cutoff of the shorter-wave range (below 460 nm) is produced in this case by a yellow dye, for example, by 200 to 3000 mg/m$^2$ of a pyrazolone derivative. The cutoff of the longer-wave range (above 480 nm) is produced by a blue dye, for example, by 200 to 3000 mg/m$^2$ of an anthraquinone derivative.

For this, either separate filters can be used, or both dyes can be incorporated together in the synthetic material, formed into a sheet or plate, or they can be applied to the synthetic to form a lacquer layer on it.

Within the scope of the invention, interference filters can also be used. In such cases, thin layers are coated (mostly by vapor deposition) on a transparent substrate (of, for example, quartz, glass, or synthetic), the nature, thickness and order of the layers being such that only radiation in the desired spectral range is reflected or transmitted. Interference-type transmission filters of the line, band, double-line, or double-band type, whose maximum transmittance lies near 470 nm can be used.

Interference filters of the reflection type are dichroic mirrors which separate the incident radiation with low loss. This arrangement permits the edge of the shorter-wave range to be shifted by changing the angle of incidence (e.g. Schott 312). The edge of the lower-wave range can likewise be shifted by changing the angle of incidence (e.g. Schott 960). A combination of the two last-named filters thus transmits selectively the desired spectral range of 460 to 480 nm. Other dichroic mirrors (e.g. Schott 930) selectively reflects this range.

From what has been said above, it follows that also combinations of the different filter types can be employed to obtain the desired radiation range of 460 to 480 nm as steeply defined as possible.

For the proper functioning of the invented radiation device, adequate cooling of the radiator and filters is essential.

For the purpose of this invention, a high-pressure radiator should be maintained during operation at a temperature between 600° and 1000° C., preferably between 700° and 800° C., whereas the optimal operating temperature for a low-pressure lamp lies in the range of 40° to 60° C. (measured in all cases at the wall of the bulb).

If the high-pressure radiator is mounted on a reflector (preferably of anode-brightened aluminium), the latter is for best operation kept at an operating temperature of 100° to 130° C. with a suitable cooling system.

With absorption filters, the operating temperature should not exceed approximately 80° C. The flow of the cooling air should be such that the strongest cooling is provided for the absorption filter that suppresses the radiation below 460 nm.

A number of embodiments of the invention are depicted in the drawing, wherein:

FIG. 1 Schematic representation of a section through a radiation device with high-pressure lamp and glass filters according to the invention.

FIG. 2 Schematic representation of a section through an embodiment of the invention using a low-pressure lamp and synthetic filters.

FIG. 3 Diagram showing the spectral power distributions of the radiation emitted by radiators.

FIG. 4 Diagram showing the spectral transmittance of filters.

FIG. 5 Diagram showing the spectral power distribution of filtered radiation.

The irradiation device represented schematically in FIG. 1 consists of a high pressure-lamp 2 contained in a housing 1 and mounted in an anode-brightened aluminium reflector 3. Filters 4, 5 and 6 are installed in that order in the radiation path.

Filter 4 is a heat-absorption filter (Schott KG1 6 mm), filter 5 is a blue glass filter (Schott BG37 5 mm) for suppressing the radiation above 480 nm, and filter 6 is a cutoff filter (Schott GG475 3 mm) for suppressing the radiation below 460 nm.

A ventilator 7 forces cooling air through the interior of the housing as shown with arrows 8, and in particular across the filters 4, 5 and 6. The cooling air leaves the housing through openings 9. The radiator 2 can, for example be a high pressure mercury lamp with cadmium-iodide and/or zinc-iodide doping. The irradiance at the irradiated area (20 inches=50 cm from the filter system) is about 20 W/m$^2$.

FIG. 2 is, in contrast, a schematic representation of an embodiment of the radiation device consisting of a number of low-pressure lamps 12, 12a, 12b and 12c contained in a housing 11. These low-pressure lamps are mounted in a reflector 13. A synthetic filter 14 is mounted in the radiation path. The inner space of the reflector 13 containing the low-pressure lamps 12 to 12c is cooled by a stream of air (which, for example, flow perpendicular to the plane of FIG. 2 parallel to the axial direction of the low-pressure lamps 12 to 12c.

The low-pressure lamps (fluorescent lamps) 12 to 12c are, for example, low-pressure mercury-vapor lamps with a phosphor consisting of barium-magnesium aluminate activated with europium, and a deposited reflecting layer 15.

For the further elucidation of the manner of operation of the two embodiments of FIGS. 1 and 2, the relative spectral radiant flux $\Phi_e$ (rel) for the two lamps of FIGS. 1 and 2 are shown in FIG. 3. Curve 1 shows the spectral emission of a low-pressure mercury lamp with phosphor consisting of barium-magnesium aluminate activated with europium.

Curve 2 shows the spectral radiant flux of a high-pressure mercury lamp doped with cadmium iodide and zinc iodide.

The curves of FIG. 3 show that both of these lamps have strong radiation components in the desired wavelength range of 460 to 480 nm, but that the portions of the radiation lying outside this range are still so considerable that filtering is required.

Figure 1:
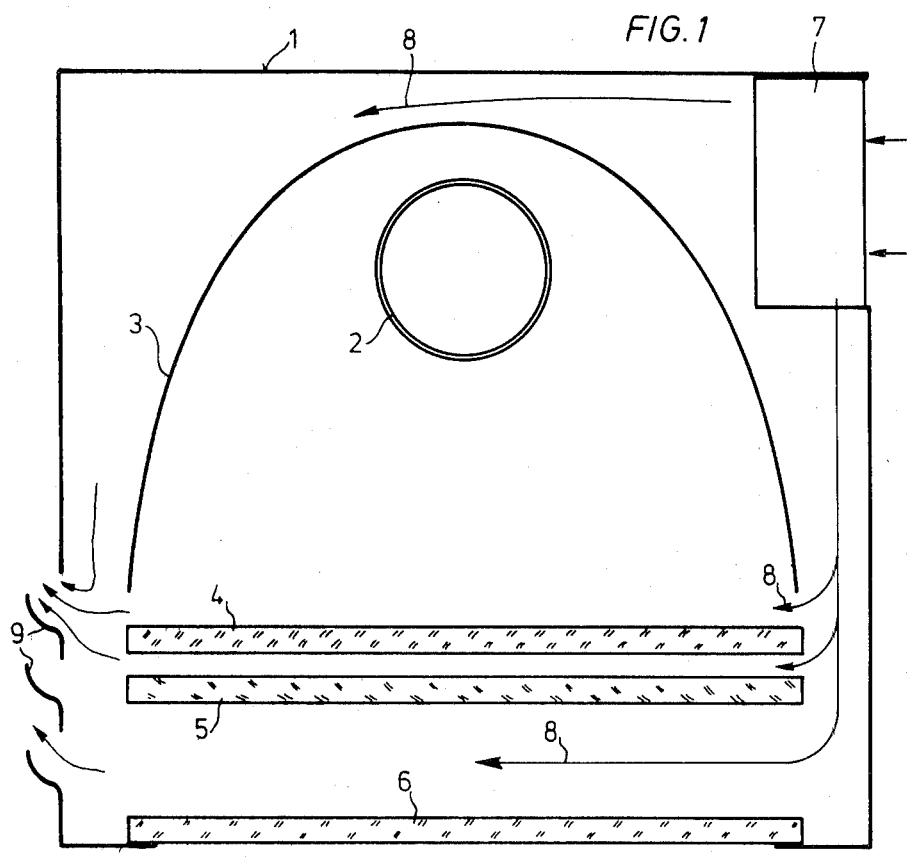
Figure 2:
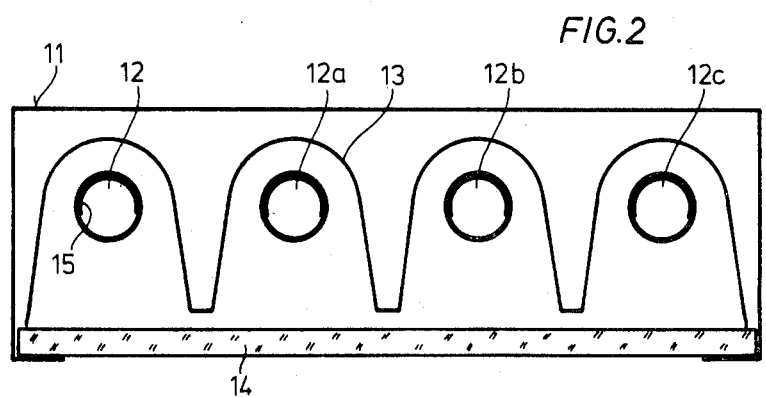
Figure 3:
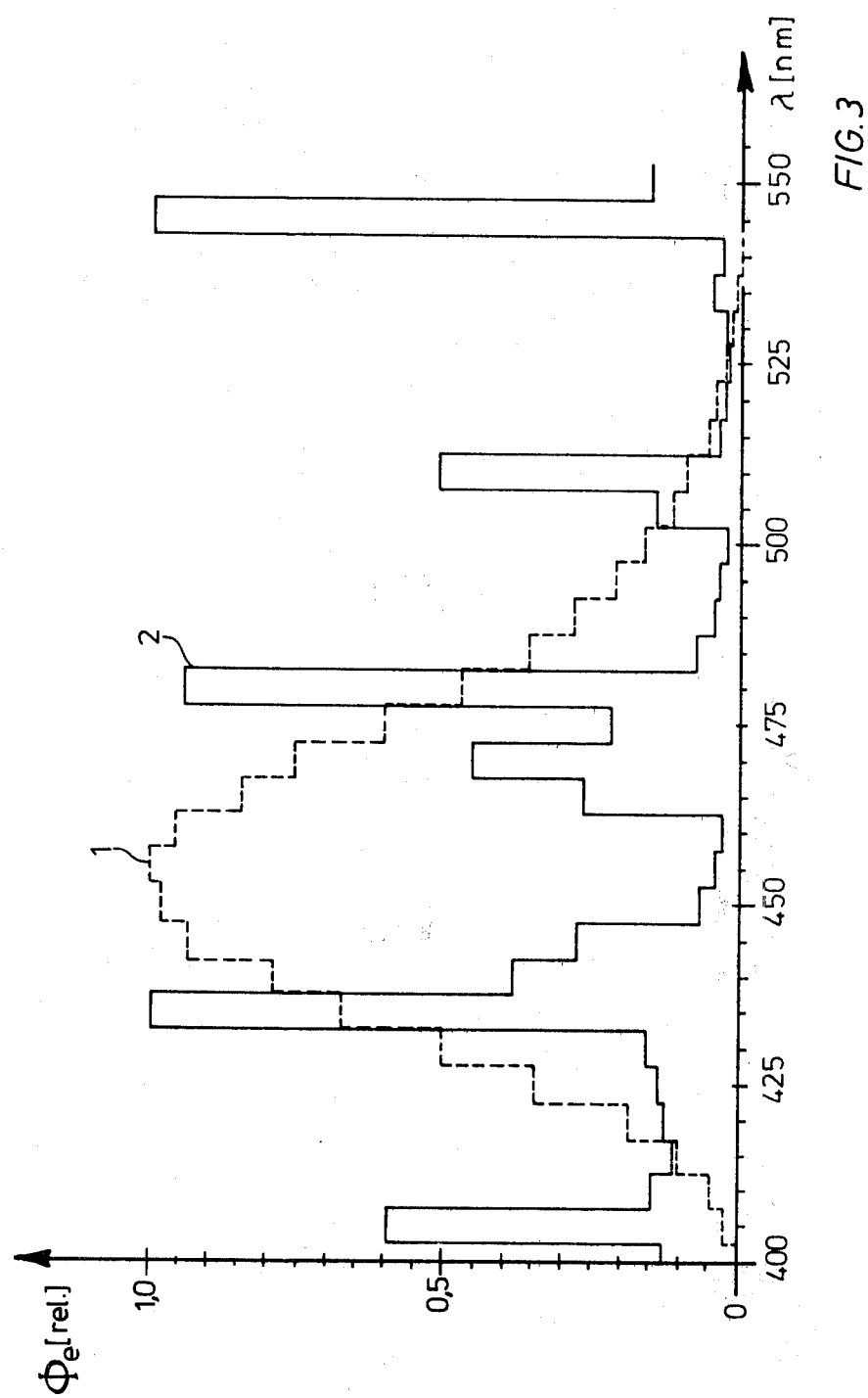
Figure 4:
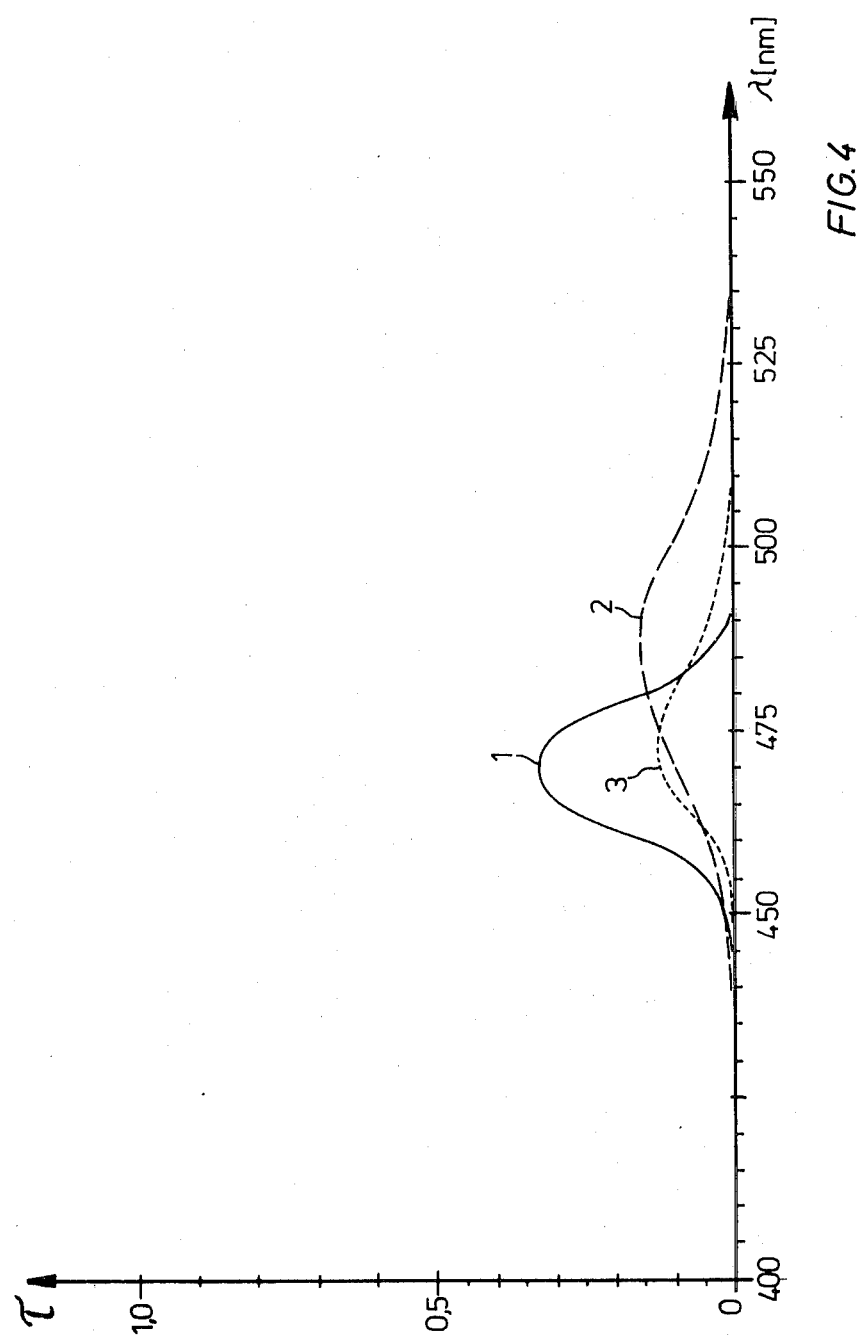
FIG. 4 shows the spectral transmittance $\tau$ of three different filter types: Curve 1 an interference filter, Curve 2 a synthetic absorption filter, and Curve 3 a glass absorption filter.
Figure 5:
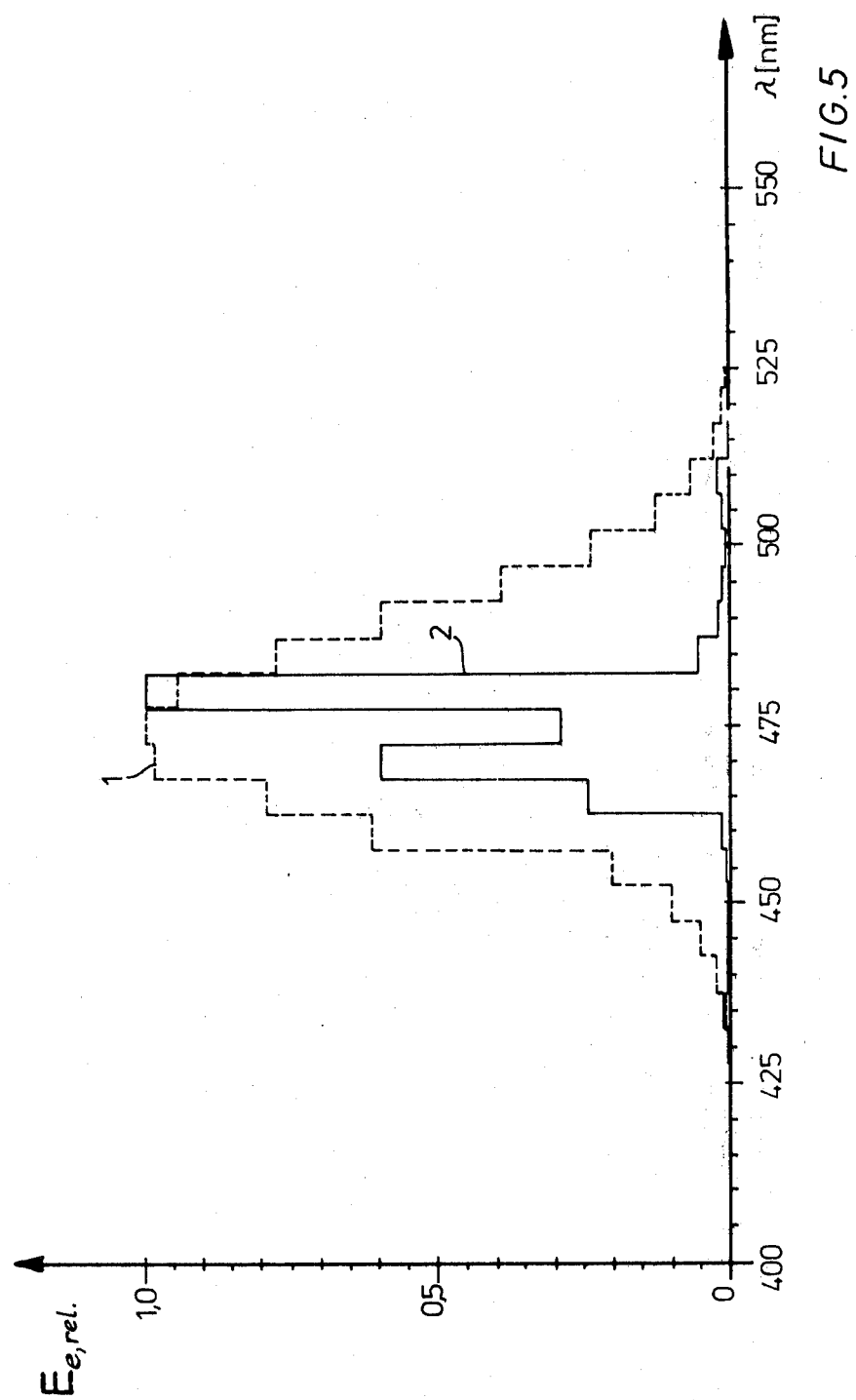
FIG. 5 shows the relative irradiance $E_{e,rel}$ at the irradiated area, on the one hand, Curve 1, when the low-pressure mercury lamp (Curve 1 of FIG. 3) is combined with the synthetic filter (Curve 2 of FIG. 4), and, on the other hand, Curve 2, when the high-pressure mercury lamp (Curve 2 of FIG. 3) is combined with the glass filter (Curve 3 of FIG. 4).

In the first case, Curve 1 of FIG. 5, the portion of the spectrum lying between 460 and 480 nm comprises about 60% of the entire emitted radiation (whereas for unfiltered radiation only 35% of the entire radiation lies in the 460-to 480 nm range).

The irradiance in the range between 460 and 480 nm is therefore about 10 W/m$^2$ for an irradiated area of 24×18 inches (60×45 cm) and a power input to the lamps about 600 W.

In the second case, Curve 2 of FIG. 5, the portion of the spectrum between 460 and 480 nm comprises about 90% of the entire emitted radiation. The irradiance in the range between 460 and 480 nm is about 20 W/m$^2$ for an irradiated area of 24×18 cm). The power input to the lamp is about 4000 W.

I claim:

1. A phototherapeutic irradiation device for the treatment of hyperbilirubinemia in newborn infants comprising radiator means for producing radiation having an effective range of between 405 and 545 nm; means for limiting to 10% at most the radiation in said range below about 460 nm; and means for directing said radiation along a path.

2. A device according to claim 1 wherein said limiting means limits at least 50% of the radiation present in the effective range to between 460 and 480 nm.

3. A device according to claim 2 wherein said limiting means limits at least 50% of the entire radiation to between 460 and 480 nm.

4. A device according to claim 3 wherein said limiting means limits at least 90% of the entire radiation to between 460 and 480 nm.

5. A device according to claim 2 wherein the capacity of said radiator means is such that the irradiance within the range 460 to 480 nm in the irradiated area is at least 2 W/m$^2$.

6. A device according to claim 2 wherein the capacity of said radiator means is such that the irradiance within the range 460 to 480 nm in the irradiated area is at least 5 to 30 W/m$^2$.

7. A device according to claim 2, wherein said radiator means comprises a low-pressure mercury lamp with a large portion of its radiation lying between 460 and 480 nm, said lamp being coated with a phosphor.

8. A device according to claim 7, wherein the low-pressure mercury lamp has a reflecting layer applied either on its interior or its exterior.

9. A device according to claim 7 wherein said phosphor is selected from the class consisting of barium-magnesium aluminate activated with europium; calcium-fluorophosphate activated with antimony; calcium tungstate activated with lead; strontium pyrophosphate activated with tin; barium-titanium pyrophosphate activated with tungsten; magnesium tungstate activated with tungsten; and strontium fluorophosphate activated with antimony and manganese.

10. A device according to claim 2 including an absorption filter of glass containing sulfur and/or cadmium sulfide in said path for the suppression of radiation of wavelengths less than 460 nm.

11. A device according to claim 2 including an absorption filter of glass containing dissolved nickel oxide in said path and/or cobalt oxide for the suppression of radiation lying above 480 nm.

12. A device according to claim 2 including a heat-absorbing filter in said path for the suppression of residual infrared radiation.

13. A device according to claim 2 including an absorption filter of snythetic material with a yellow dye, having 200 to 3000 mg/m$^2$ of pyrazolone derivative in said path for the suppression of radiation lying below 460 nm.

14. A device according to claim 2 including an absorption filter of synthetic material with a blue dye having 200 to 3000 mg/m$^2$ of anthraquinone derivate in said path for the suppression of radiation above 480 nm.

15. A device according to claim 1 wherein said radiator means comprises a low-pressure mercury lamp coated with a phosphor and having a high portion of its radiation between 460 and 480 nm and in which an amalgam is used in place of elementary mercury.

16. A device according to claim 15 wherein said amalgam is indium.

17. A device according to claim 1 wherein said radiator means comprises a high-pressure mercurcy lamp doped with a rare earth halide of the class consisting of cadmium halide, zinc halide, and thulium halide.

18. A device according to claim 17 wherein the high-pressure mercury lamp is doped with 0.01 to 4 mg/cm$^3$ of said halide.

19. A device according to claim 18 including reflector means adjacent said lamp and cooling means for maintaining said lamp during operation at a temperature of between 600° and 1000° C., and the reflector means at a temperature of between 100° and 130° C.

20. A device according to claim 19 wherein said cooling means maintains said lamp during operation at a temperature of between 700° and 800° C.

21. A device according to claim 1 wherein said radiator means comprises a high-pressure lamp doped with a rare earth halide of the class consisting of cadmium halide, zinc halide, and thulium halide, and free of mercury.

22. A device according to claim 21 wherein said radiator means contains 0.02 to 8 mg/cm$^3$ of said halide.

23. A device according to claim 1 including an absorption filter in said path and cooling means operable during operation of said radiator means to maintain the absorption filter at a temperature of about 80° C. maximum.

24. A device according to claim 1 including a number of absorption filters in said path one of which is for suppression of said radiation below 460 nm, and cooling means so directed that said one absorption filter is maintained cooler than any other of said filters.

* * * * *

UNITED STATES PATENT AND TRADEMARK OFFICE
CERTIFICATE OF CORRECTION

PATENT NO. : 4,444,190
DATED : April 24, 1984
INVENTOR(S) : Maximilian F. Mutzhas It is certified that error appears in the above-identified patent and that said Letters Patent are hereby corrected as shown below:

Column 1, line 26, before "405" insert -- (preferably --.

Column 1, line 44, change "objectives" to -- objective --.

Column 5, line 27, after "18" insert -- inches (60 x 45 --.

Column 5, line 33, after "nm" insert -- and --.

Column 6, line 11, change "in said path and/or cobalt oxide" to -- and/or cobalt oxide in said path -- .

Signed and Sealed this

Thirtieth Day of October 1984

[SEAL]

Attest:

GERALD J. MOSSINGHOFF

Attesting Officer    Commissioner of Patents and Trademarks